(12) United States Patent
Nakamura

(10) Patent No.: US 10,803,986 B2
(45) Date of Patent: Oct. 13, 2020

(54) AUTOMATIC LAYOUT APPARATUS, AUTOMATIC LAYOUT METHOD, AND AUTOMATIC LAYOUT PROGRAM

(71) Applicant: FUJIFILM Corporation, Tokyo (JP)

(72) Inventor: Keigo Nakamura, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 218 days.

(21) Appl. No.: 15/950,830

(22) Filed: Apr. 11, 2018

(65) Prior Publication Data

US 2018/0301216 A1 Oct. 18, 2018

(30) Foreign Application Priority Data

Apr. 12, 2017 (JP) ................. 2017-078960

(51) Int. Cl.
*G06K 9/00* (2006.01)
*G16H 30/40* (2018.01)
(Continued)

(52) U.S. Cl.
CPC ........... *G16H 30/40* (2018.01); *A61B 5/7425* (2013.01); *A61B 6/566* (2013.01); *A61B 8/565* (2013.01); *G06F 16/50* (2019.01); *G06F 16/51* (2019.01); *G06K 9/6212* (2013.01); *G06T 7/0014* (2013.01); *G06T 11/00* (2013.01); *G16H 30/20* (2018.01); *A61B 5/055* (2013.01); *A61B 6/46* (2013.01); *A61B 8/46* (2013.01); *G06T 2207/10088* (2013.01)

(58) Field of Classification Search
CPC ........ G16H 30/40; G16H 30/20; G06F 16/50; G06K 9/6212; A61B 5/055; G06T 7/0014; G06T 2207/10088
See application file for complete search history.

(56) References Cited

U.S. PATENT DOCUMENTS

| 8,837,794 B2 | 9/2014 | Nakamura |
| 2003/0018245 A1* | 1/2003 | Kaufman ............... A61B 6/463 600/407 |

(Continued)

FOREIGN PATENT DOCUMENTS

| EP | 3388962 A1 * | 10/2018 | ............ G06F 19/00 |
| JP | 2004-160103 A | 6/2004 | |

(Continued)

OTHER PUBLICATIONS

Masato Mori, "A New Picture Hanging Protocol in Image Viewing of PACS", NAIST-IS-DT9961206, pp. 35-50 (Jan. 29, 2003).

(Continued)

*Primary Examiner* — Shefali D Goradia
(74) *Attorney, Agent, or Firm* — Sughrue Mion, PLLC

(57) ABSTRACT

Reception means receives examination data including a plurality of examination images. Similar examination data specifying means specifies sample examination data similar to the examination data using a similarity between each examination image included in the examination data and each sample image included in the sample examination data. Display means displays the examination image included in the examination data according to layout information associated with the sample examination data similar to the examination data.

12 Claims, 12 Drawing Sheets

(51) Int. Cl.
*G16H 30/20* (2018.01)
*G06T 7/00* (2017.01)
*G06K 9/62* (2006.01)
*G06F 16/50* (2019.01)
*A61B 5/00* (2006.01)
*G06F 16/51* (2019.01)
*G06T 11/00* (2006.01)
*A61B 8/00* (2006.01)
*A61B 6/00* (2006.01)
*A61B 5/055* (2006.01)

(56) References Cited

U.S. PATENT DOCUMENTS

| | | | |
|---|---|---|---|
| 2009/0213034 A1* | 8/2009 | Wu | G16H 30/20 |
| | | | 345/1.1 |
| 2010/0061634 A1* | 3/2010 | Howie | G06F 16/313 |
| | | | 382/176 |
| 2010/0123831 A1* | 5/2010 | Crucs | A61C 9/004 |
| | | | 348/715 |
| 2013/0324849 A1* | 12/2013 | Park | A61B 8/13 |
| | | | 600/440 |
| 2015/0317434 A1* | 11/2015 | Kondo | G06F 16/24 |
| | | | 705/3 |
| 2018/0293772 A1* | 10/2018 | Akahori | G06T 7/97 |
| 2018/0293773 A1* | 10/2018 | Kohle | A61B 6/463 |

FOREIGN PATENT DOCUMENTS

| | | |
|---|---|---|
| JP | 2007-260061 A | 10/2007 |
| JP | 2007-275216 A | 10/2007 |
| JP | 2007-286945 A | 11/2007 |
| JP | 2011-041585 A | 3/2011 |
| JP | 5670079 B2 | 2/2015 |
| JP | 2018-175864 A | 11/2018 |

OTHER PUBLICATIONS

Office Action dated Aug. 18, 2020 in Japanese Application No. 2017-078960 English Translation.

* cited by examiner

AUTOMATIC LAYOUT APPARATUS, AUTOMATIC LAYOUT METHOD, AND AUTOMATIC LAYOUT PROGRAM

CROSS-REFERENCE TO RELATED APPLICATION

This application claims priority from Japanese Patent Application No. 2017-078960, filed on Apr. 12, 2017, the disclosure of which is incorporated by reference herein in its entirety.

BACKGROUND

Field of the Invention

The present invention relates to a display protocol for assisting image interpretation, and more particularly, an automatic layout apparatus, an automatic layout method, and an automatic layout program for automatically laying out images.

Related Art

In recent years, with the spread of medical information systems, a wide-area electronic medical record allowing the exchange of data between medical institutions for the purpose of cooperation in disease diagnosis and sharing of medical information in the community has been realized. As elemental technologies of the wide-area electronic medical record system, there is a picture archiving and communication system (PACS) provided in each medical institution. In the PACS, storage, viewing, and management of image data received from image capturing apparatuses (modalities), such as computed radiography (CR) apparatuses, computed tomography (CT) apparatuses, and magnetic resonance imaging (MRI) apparatuses, are performed. In addition, by managing image data using a digital imaging and communication in medicine (DICOM) standard, unified management of various types of image data has become possible.

In the image examination, a plurality of images (a simple X-ray image, a CT image, an MRI image, an ultrasound image, and the like) are captured for one patient, the captured images are read out from the PACS, and the read images are displayed on the screen of an interpretation viewer or the like so as to be able to be checked. In order for a radiologist to efficiently observe these medical images, an apparatus is known in which a display protocol defining a screen layout (screen division number, tile display, stack display, and the like) or the display position of a display target image for each modality is set in advance so that image display according to the needs of the radiologist can be realized and an image to be interpreted is displayed based on a display protocol selected by the radiologist at the time of interpretation.

As a specific display protocol, for example, a method of arranging images in the imaging order or a method of arranging images according to a rule defined based on information (DICOM tag information or the like) attached to the images is known. For example, JP2007-260061A discloses a method in which definition information, which defines the arrangement order of a plurality of medical images using supplementary information of the medical images, is used and the medical images are displayed so as to be arranged at positions defined according to the definition information using the supplementary information of the medical images in the case of simultaneously displaying the plurality of medical images on the screen. JP5670079B discloses a method of extracting information regarding an anatomical structure and a lesion in findings from interpretation report information and determining an optimal display protocol based on the information.

In principle, the display order of images follows the generation time of each captured image as much as possible. However, in the case of wasting the display, a slight change of the display order is allowed as long as an image can be efficiently determined. In addition, a display protocol allowing images to be arranged on as few pages as possible and efficiently observable is desired. In order to determine such a protocol, a method of preparing a pattern in the case of arranging a plurality of screens based on the resolution and determining a display protocol by determining the optimum degree of the display protocol from the resolution, order, and screen usage rate so that a region where anything useless is displayed on the screen is reduced in consideration of the order in which examination images are generated is disclosed in Masato Mori "A New Picture Hanging Protocol in Image Viewing of PACS", NAIST-IS-DT9961206, p 35-50.

In order to quickly determine an examination image, performing image display according to the case or the radiologist's preference is important in improving interpretation efficiency. In a case where a medical information system in which a plurality of medical institutions cooperate with each other, such as a wide-area electronic medical record system, is constructed, a request for interpretation of an image captured in each medical institution is sent to a medical institution that has a radiologist specializing in interpretation. However, the description of supplementary information, such as the imaging order or the DICOM tag attached to the image, is not standardized. Accordingly, in a case where the vendor (manufacturer) of an imaging apparatus or the imaging technician is different, images may be captured in different imaging order, or the method of describing tag information may be different. For this reason, there is a problem that the method disclosed in JP2007-260061A does not appropriately function. In particular, since information regarding images different depending on the imaging conditions, such as a T1-weighted image and a T2-weighted image of an MRI image, is not standardized, there is a high possibility that the images will not be arranged at appropriate display positions.

As in JP5670079B, in a case where there is an interpretation report of a past examination, it is possible to select an optimal display protocol with reference to information described in the interpretation report. In addition, by extracting a keyword by performing natural language analysis on the interpretation report, it is also possible to determine an optimal display protocol. However, in a situation where there is no past interpretation report, it is not possible to determine what kind of display protocol is optimal. Even in a case where there are anatomical structures or similar lesions, it is difficult to determine the optimal display protocol under different pieces of examination data.

A method of determining a display protocol for efficient display is described in Masato Mori "Research on optimum hanging protocol in PACS image display", NAIST-IS-DT9961206, p 35-50. However, in the case of performing accurate diagnosis, it is necessary to set a layout suitable for diagnosis, and this point is not taken into consideration.

SUMMARY

Therefore, in order to solve the aforementioned problem, it is an object of the invention to provide an automatic layout apparatus, an automatic layout method, and an automatic layout program for automatically laying out examination images with a display protocol optimal for interpretation.

An automatic layout apparatus of the invention comprises: reception means for receiving examination data including a plurality of examination images; connection means for being connected to a storage unit that stores layout information, which indicates a layout in which sizes and arrangement positions of a plurality of sample images in a case of arranging the sample images on a screen are set, so as to be associated with sample examination data including the plurality of sample images; similar examination data specifying means for specifying the sample examination data similar to the examination data using a similarity between each examination image included in the examination data and each sample image included in the sample examination data; and display means for displaying the examination image included in the examination data according to layout information associated with the sample examination data similar to the examination data.

An automatic layout method of the invention is an automatic layout method in an automatic layout apparatus comprising reception means, connection means, similar examination data specifying means, and display means, and comprises: a reception step in which the reception means receives examination data including a plurality of examination images; a connection step in which the connection means is connected to a storage unit that stores layout information, which indicates a layout in which arrangement positions where a plurality of sample images are arranged on a screen are set, so as to be associated with sample examination data including the plurality of sample images; a similar examination data specifying step in which the similar examination data specifying means specifies the sample examination data similar to the examination data using a similarity between each examination image included in the examination data and each sample image included in the sample examination data; and a display step in which the display means displays the examination image included in the examination data according to layout information associated with the sample examination data similar to the examination data.

An automatic layout program of the invention causes a computer to function as: receiving means for receiving examination data including a plurality of examination images; connection means for being connected to a storage unit that stores layout information, which indicates a layout in which sizes and arrangement positions of a plurality of sample images in a case of arranging the sample images on a screen are set, so as to be associated with sample examination data including the plurality of sample images; similar examination data specifying means for specifying the sample examination data similar to the examination data using a similarity between each examination image included in the examination data and each sample image included in the sample examination data; and display means for displaying the examination image of the examination data according to layout information associated with the sample examination data similar to the examination data.

"Layout information" refers to information including a screen division method and image arrangement positions at the time of arranging images on the screen. The screen division method includes, for example, a method of dividing the screen into two regions, four regions, or the like and the size of each divided region.

"Examination data" refers to data necessary for diagnosing a disease, and includes a plurality of examination images. The examination images include still images and motion pictures captured by various modalities. The examination image may be an image obtained by converting document data regarding the examination.

"Sample examination data" refers to examination data including a sample image serving as a sample in a case where an examination image of new examination data is arranged. The sample image refers to an image serving as a sample of an examination image to be arranged on the layout.

The examination data and the sample examination data may include images captured by different types of modalities, and the similar examination data specifying means may acquire the similarity by associating the sample image and the examination image captured by the same type of modality with each other.

The examination data and the sample examination data may include images captured by different types of imaging protocols of a magnetic resonance imaging apparatus.

The similar examination data specifying means may comprise similarity acquisition means for acquiring a similarity between the examination image and the sample image for each combination of one of sample images included in the sample examination data and one of examination images included in the examination data. In a case where the examination image and the sample image are associated with each other so as to satisfy conditions in which the number of sample images associated with the examination image in the examination data is one or less and the number of examination images associated with the sample image is one or less, the similar examination data specifying means may specify sample examination data similar to the examination data according to a predetermined rule using all the similarities acquired by the similarity acquisition means in a combination of the examination image and the sample image associated with each other.

It is preferable that the similar examination data specifying means sets a weighting coefficient based on a display position on a layout of each sample image included in the sample examination data and specifies the sample examination data similar to the examination data using a similarity obtained by multiplying a similarity between each examination image and each sample image by the weighting coefficient of the sample image.

It is preferable that the similar examination data specifying means further comprises adjustment value acquisition means for acquiring an adjustment value of the similarity based on a relationship between an imaging time of an examination image included in a first combination of two combinations and an imaging time of an examination image included in a second combination and a relationship between an imaging time of a sample image included in the first combination and an imaging time of a sample image included in the second combination. It is preferable that, in a case where the examination image and the sample image are associated with each other so as to satisfy the conditions, the similar examination data specifying means specifies sample examination data similar to the examination data according to a predetermined rule using all the similarities acquired by the similarity acquisition means in a combination of the sample image and the examination image associated with each other and all the adjustment values acquired by the adjustment value acquisition means in the two combinations.

It is preferable that, in a case where an order of imaging times of a sample image included in the first combination and a sample image included in the second combination is the same as an order of imaging times of an examination image included in the first combination and an examination image included in the second combination, the adjustment value acquisition means sets a value to increase the similarity as the adjustment value.

It is preferable that a tomographic image is included in a sample image of the layout and a tomographic image is included in an examination image of the examination data. It is preferable that the similar examination data specifying means comprises adjustment value acquisition means for acquiring an adjustment value of the similarity based on a relationship between a tomographic position of a sample image included in a first combination of two combinations and a tomographic position of a sample image included in a second combination and a relationship between a tomographic position of an examination image included in the first combination and a tomographic position of an examination image included in the second combination. It is preferable that, in a case where the sample image and the examination image are associated with each other so as to satisfy the conditions, the similar examination data specifying means specifies sample examination data similar to the examination data according to a predetermined rule using all the similarities acquired by the similarity acquisition means in a combination of the sample image and the examination image associated with each other and all the adjustment values acquired by the adjustment value acquisition means in the two combinations.

It is preferable that, in a case where an order of tomographic positions of a sample image included in the first combination and a sample image included in the second combination is the same as an order of tomographic positions of an examination image included in the first combination and an examination image included in the second combination, the adjustment value acquisition means sets a value to increase the similarity as the adjustment value.

The similarity acquisition means may acquire the similarity based on a histogram of the examination image and the sample image.

The examination data may include one or more pieces of electronic document data, and the similar examination data specifying means may specify the sample examination data similar to the examination data based on whether or not a similar keyword is included in electronic document data of the examination data and electronic document data of the sample image data.

According to the invention, since the layout information indicating the layout of a plurality of sample images is stored so as to be associated with the sample examination data including the sample images, sample examination data similar to the examination data is specified, and examination images included in the examination data are displayed according to the layout information associated with the sample examination data, it is possible to automatically display a new examination image in the same layout as a similar case. As a result, it is possible to improve working efficiency.

DETAILED DESCRIPTION

Figure 1:
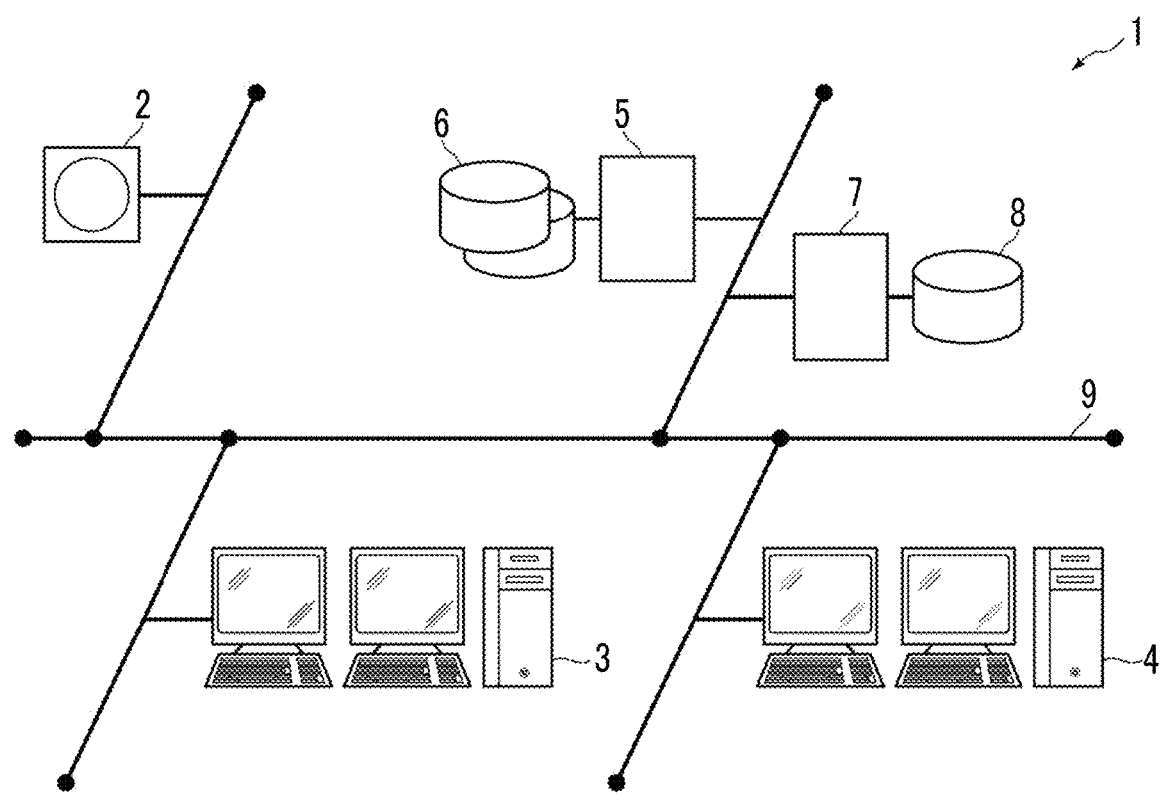
FIG. 1 is a diagram showing the schematic configuration of a medical information system in which an automatic layout apparatus according to an embodiment of the invention is introduced.

FIG. 1 shows the schematic configuration of a medical information system 1 in which an automatic layout apparatus according to an embodiment of the invention is introduced. The medical information system 1 is a system for performing imaging of an examination target part of a subject and storage of the obtained image, interpretation of an image captured by a radiologist in a radiology department and creation of an interpretation report, and viewing of an interpretation report by a doctor in a medical department of a requester and detailed observation of an image to be interpreted, based on an examination order from a doctor of a medical department using a known ordering system. As shown in FIG. 1, the medical information system 1 is configured to include a modality 2, a workstation for radiologists 3, a medical department workstation 4, an image management server 5, an image database 6, an interpretation report server 7, and an interpretation report database 8 that are communicably connected to each other through a network 9. An application program for causing each apparatus to function as a component of the medical information system 1 is installed. The application program may be installed from a recording medium, such as a CD-ROM, or may be installed after being downloaded from a storage device of a server connected through a network, such as the Internet.

The modality 2 includes an apparatus that generates an examination image showing an examination target part of a subject by imaging the examination target part of the subject, adds supplementary information specified by the DICOM standard to the examination image, and outputs the examination image. As specific examples, a CT apparatus, an MRI apparatus, a positron emission tomography (PET) apparatus, an ultrasound apparatus, and a CR apparatus using a planar X-ray detector (flat panel detector; FPD) can be mentioned.

The workstation for radiologists 3 is a computer used by a radiologist in the radiology department for image interpretation and creation of an interpretation report, and has a known hardware configuration, such as a central processing unit (CPU), a main storage device, an auxiliary storage device, an input and output interface, a communication interface, an input device, a display device, and a data bus. A known operating system or the like is installed on the workstation for radiologists 3, and one or a plurality of high-definition displays are provided as a display device. In the workstation for radiologists 3, each process, such as an image transmission request to the image management server 5, display of an image received from the image management server 5, automatic detection and highlighting of a lesion-like portion in an image, and creation and display of an interpretation report, is performed by executing a software program for each process. In addition, the workstation for radiologists 3 transmits the created interpretation report to the interpretation report server 7 through the network 9, and makes a request for registration of the interpretation report in the interpretation report database 8.

The medical department workstation 4 is a computer used by a doctor in the medical department for detailed observation of images or viewing of interpretation reports and for viewing and inputting of electronic medical records, and has a known hardware configuration, such as a CPU, a main storage device, an auxiliary storage device, an input and output interface, a communication interface, an input device, a display device, and a data bus. A known operating system or the like is installed on the medical department workstation 4, and one or a plurality of high-definition displays are provided as a display device. In the medical department workstation 4, each process, such as an image viewing request to the image management server 5, display of an image received from the image management server 5, automatic detection or highlighting of a lesion-like portion in an image, an interpretation report viewing request to the interpretation report server 7, and display of an interpretation report received from the interpretation report server 7, is performed by executing a software program for each process. In addition, the medical department workstation 4 transmits a motion picture in an endoscopic examination or the like performed in each medical department to the image management server 5 through the network 9, and makes a request for registration of the motion picture in the image database 6.

The image management server 5 has a software program for providing a function of a data base management system (DBMS) to a general-purpose computer. The image management server 5 includes a large capacity storage in which the image database 6 is formed. This storage may be a large capacity hard disk device connected to the image management server 5 through a data bus, or may be a disk device connected to a storage area network (SAN) or a network attached storage (NAS) connected to the network 9.

In the image database 6, examination images obtained by imaging a plurality of patients with the modality 2 and supplementary information are registered. The supplementary information includes, for example, an image identification (ID) for identifying each image, a patient ID for identifying a subject, an examination ID for identifying an examination, a unique identification (UID) allocated for each medical image, examination date and examination time at which the medical image is generated, the type of a modality used in an examination for acquiring the medical image, patient information such as patient's name, age, and gender, an examination part (imaging part), imaging conditions (whether or not a contrast medium is used, radiation dose, and the like), and information such as a series number in a case where a plurality of tomographic images are acquired in one examination.

In a case where a viewing request from the workstation for radiologists 3 is received through the network 9, the image management server 5 searches for the examination image registered in the image database 6 and transmits the extracted examination image to the workstation for radiologists 3 that is an examination image request source.

The interpretation report server 7 has a software program for providing a function of a data base management system (DBMS) to a general-purpose computer. In a case where an interpretation report registration request from the workstation for radiologists 3 is received, the interpretation report server 7 arranges the interpretation report in a database format and registers the interpretation report in the interpretation report database 8.

In the interpretation report database 8, information including, for example, an image ID for identifying an interpretation target image or a representative image, a radiologist ID for identifying an image diagnostician who performed the interpretation, position information of a region of interest, findings, and certainty of findings is registered. In addition, an examination number and a patient number acquired by referring to supplementary information of image information at the time of image interpretation can be registered. Furthermore, a reduced image of an examination image of the interpretation target image or the representative image can also be registered. In this case, it is preferable that link information for enabling access to the examination image registered in the image database 6 (address, folder name, file name, and the like of image data registered in the image database 6), which is the basis of generation of the reduced image, is also registered in the interpretation report database 8.

The network 9 is a local area network that connects various apparatuses in a hospital. In a case where the workstation for radiologists 3 is installed in another hospital or clinic, the network 9 may be configured to connect local area networks of respective hospitals through the Internet or a dedicated circuit. In any case, the network 9 is preferably a network capable of realizing high-speed transfer of medical images, such as an optical network.

Figure 13:
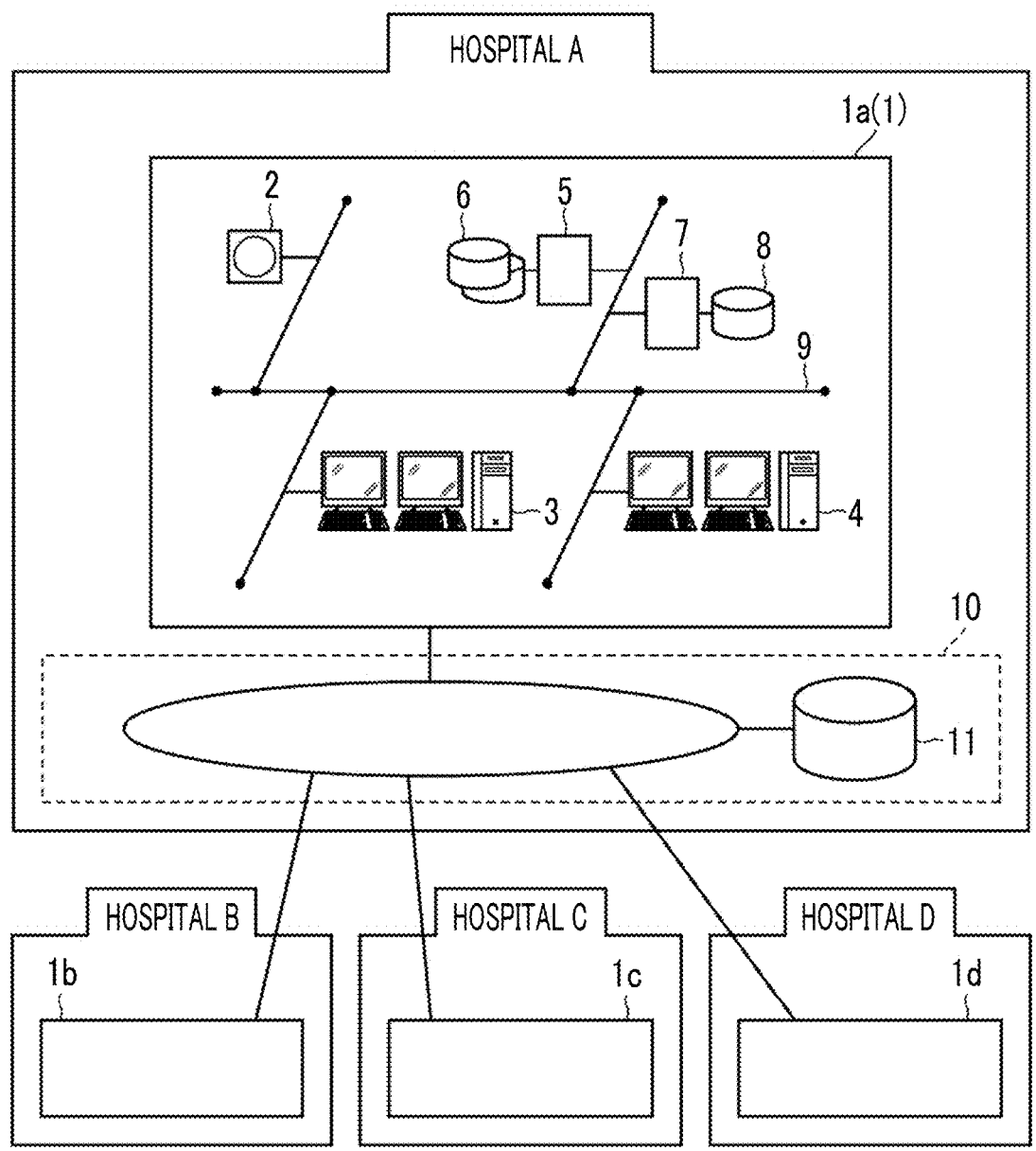
FIG. 13 is a diagram showing a schematic configuration in which an archive system is connected to a medical information system.

As shown in FIG. 13, an archive system 10 may be connected to the medical information system 1. The archive system 10 includes a large-capacity storage device 11 for storing and managing not only medical images or various motion pictures of medical information systems 1a to 1d in a plurality of medical institutions but also a wide range of clinical information, such as an examination request document (examination order) describing the examination purpose and the like handled by each department in the medical institution and a document obtained by converting other kinds of examination information, such as a blood test result, as an electronic document.

In a case where a user, such as an image diagnostician, performs an operation of making a request for interpretation and viewing of the observation target image, the workstation for radiologists 3 transmits a viewing request to the image management server 5 and acquires a required image. Then, the image is displayed on a display. The workstation for radiologists 3 has a function of the automatic layout apparatus of the invention, and this processing is realized by executing the installed application program.

Figure 2:
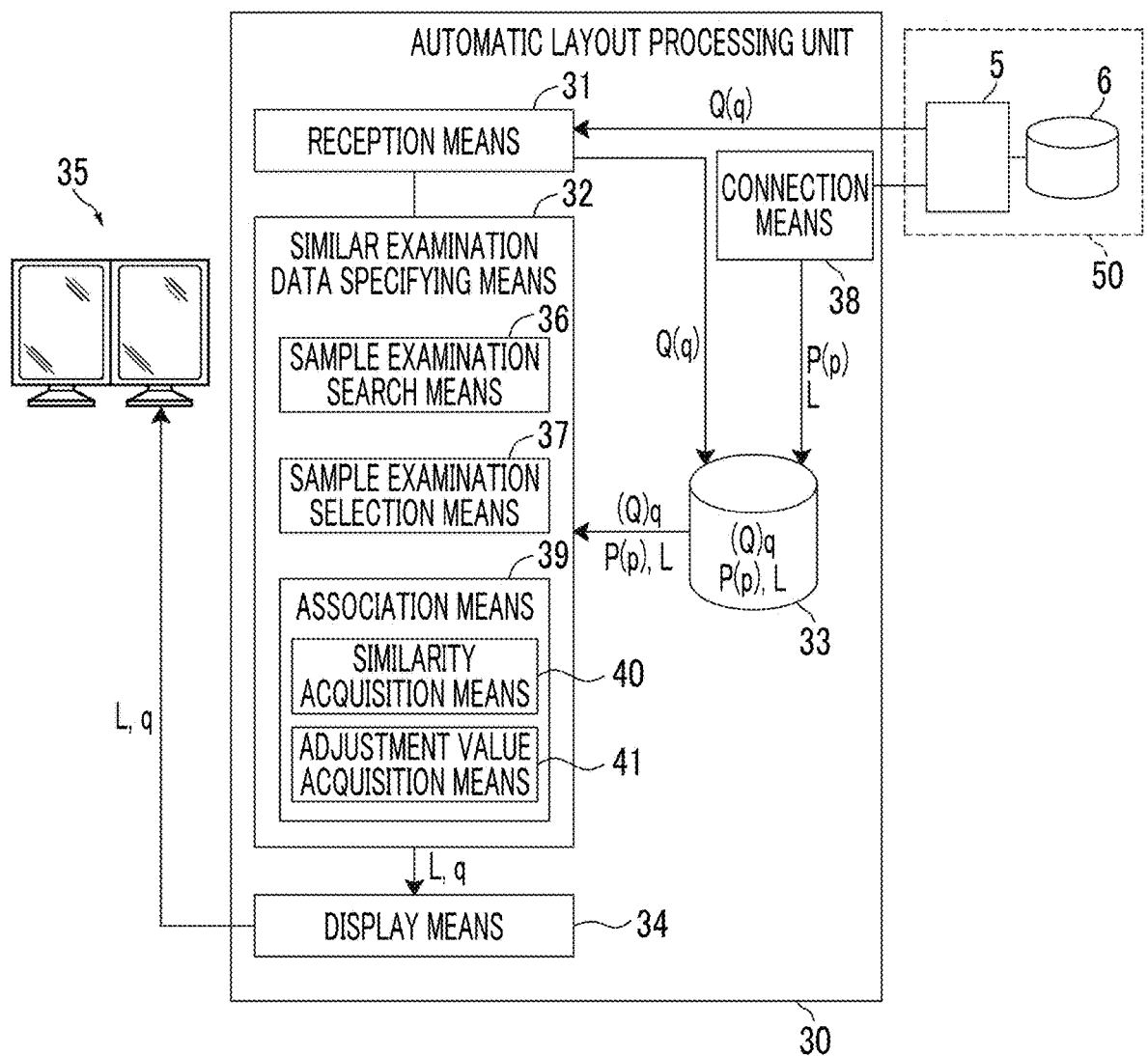
FIG. 2 is a functional block diagram of the automatic layout apparatus of the invention.

FIG. 2 is a block diagram schematically showing the configuration of the automatic layout apparatus according to the embodiment of the invention, which is mounted in the workstation for radiologists 3, and the flow of data. The automatic layout apparatus of the invention will be described below as an automatic layout processing unit of the workstation for radiologists 3. As shown in FIG. 2, an automatic layout processing unit 30 of the invention is configured to include reception means 31, connection means 38, similar examination data specifying means 32, and display means 34. One or a plurality of displays 35 are connected to the display means 34. The image management server 5 and the image database 6 that are connected to the workstation for radiologists 3 through the network 9 function as a storage unit 50 of the invention.

In the workstation for radiologists 3, in a case where the patient ID of an examination target is input by the user, such as a radiologist, the patient ID of the examination target and a viewing request are transmitted to the image management server 5, and the reception means 31 receives a plurality of examination images q searched for from the image database 6 as examination data Q. The received examination images q are temporarily stored in an auxiliary storage device 33 of the workstation for radiologists 3.

The connection means 38 is connected to the storage unit 50, and has a function of transmitting and receiving data, such as a sample image p of sample examination data P and layout information L. Although access to the storage unit 50 is performed through the network 9 and the connection means 38, the following explanation will be given on the assumption that data is simply read from and written into the storage unit 50.

The examination images q include images obtained by imaging using various modalities 2. Simple X-ray images, a current image and a past image obtained by imaging the same part, images before and after administration of a contrast medium, a plurality of tomographic images (such as CT images or MRI images), images captured with different imaging protocols (such as T1 weighting and T2 weighting of MRI images), motion pictures captured by an endoscope, and the like are included in the examination images q.

The storage unit 50 stores a plurality of sample images p and a plurality of pieces of layout information L defining arrangement positions for arranging the sample images p on the screen. In the layout information L, information regarding a screen division method at the time of arranging images on the screen and information regarding which sample image p is to be arranged in each of the divided regions are defined. The information of the screen division method also includes the size of each of the divided display regions. For example, information for vertically dividing the screen into two left and right regions so as to have the same size, information for vertically and horizontally dividing the screen into four regions so as to have the same size, or information for displaying the main image on the left half of the screen so as to be large and displaying the remaining images vertically on the right half is defined. The sample image p is an image serving as a sample in the case of arranging the examination images q on the screen, and is an image serving as a reference in the case of arranging examination images of a patient to be examined.

For example, in a case where the radiologist performs interpretation at the workstation for radiologists 3, recorded information of a screen division method and the arrangement position of each examination image at the time of observing examination images of a certain patient, which are arranged side by side on the screen of the display 35, is assumed to be the layout information L. The examination images arranged on the screen at that time are the sample images p, and the sample examination data P including the sample images p and the layout information L are stored in the storage unit 50 through the network 9 so as to be associated with each other. In the storage unit 50, a large number of sample examination data P, which have been interpreted by the radiologist in the past, and layout information are stored so as to be associated with each other.

The layout may be a single screen or a plurality of screens. For example, the layout may be configured to include a plurality of pages, and a screen division method and the arrangement position of each sample image p in the case of displaying a plurality of pages in which the sample image p is arranged on the display screen while switching the plurality of pages may be defined as the layout information L. Alternatively, the layout information L may define a screen division method of each of screens of a plurality of displays and the arrangement position of each sample image p in a case where the plurality of displays are connected to the workstation for radiologists 3. For example, on a single display, a combination of a screen division method of a certain page and the sample image p arranged in each divided region and a screen division method of the next page and the sample image p arranged in each divided region may be one piece of layout information L. In addition, on two or more displays, information indicating that the screen is divided into four regions in a display A and which sample image p is to be arranged in each divided region and indicating that the screen is divided into two regions in a display B and which sample image p is to be arranged in each divided region may be one piece of layout information L. In addition, information of a screen division method in the case of displaying display screens of a plurality of pages on a plurality of displays while switching the display screens and the sample image p arranged on each divided region may be one piece of layout information L.

Figure 3A:
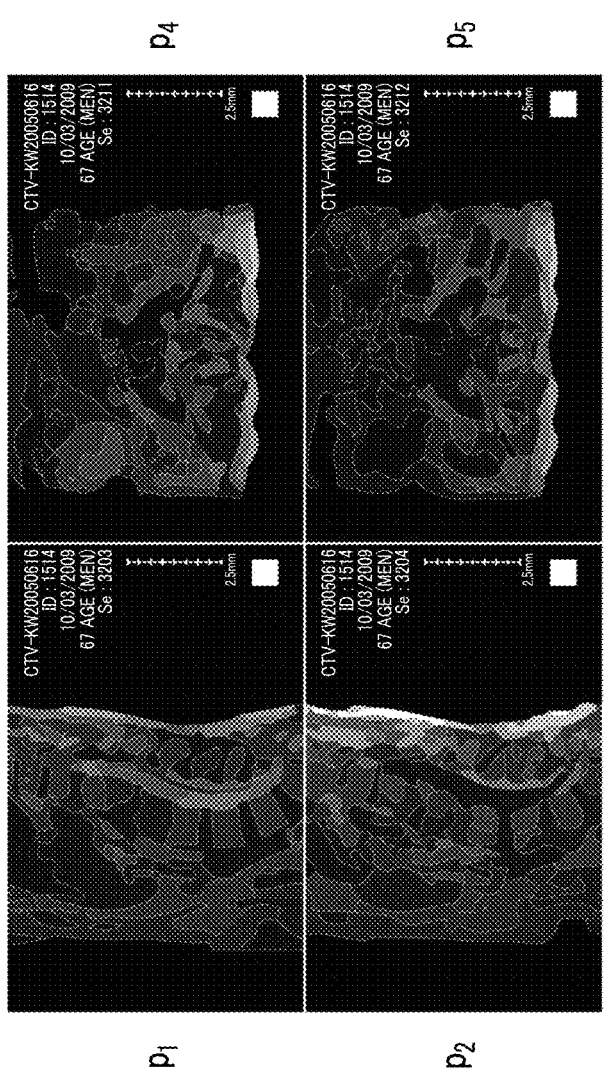
FIGS. 3A and 3B are diagrams showing examples of a layout in which sample image are arranged.
Figure 3B:
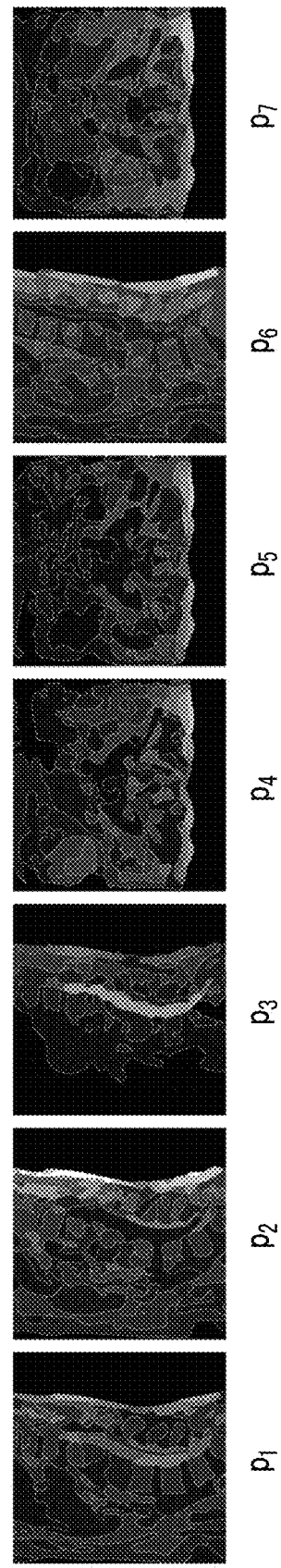

FIG. 3A shows an example of a layout in which the sample images p are arranged according to the layout information L. FIG. 3B shows sample images $p_1$ to $p_7$ arranged in respective regions of the layout. In FIG. 3A, the screen is divided into four regions, the sample image $p_1$ is arranged in the upper left region, a sample image $p_2$ is arranged in the lower left region, the sample image $p_4$ is arranged in the upper right region, and the sample image $p_5$ is arranged in the lower right region. In FIG. 3A, the sample images $p_3$, $p_6$, and $p_7$ are not displayed on the screen, but the sample images $p_3$, $p_6$, and $p_7$ may be arranged on the next page.

The similar examination data specifying means 32 includes sample examination search means 36, sample examination selection means 37, and association means 39, and specifies the sample examination data P similar to the examination data Q. The reading and writing of the sample examination data P and the layout information L are performed through the connection means 38 and the network 9, and are stored in the auxiliary storage device 33 as necessary.

The sample examination data P is narrowed down in order of (1) to (3) below.

(1) First, the sample examination search means 36 searches for the sample examination data P, which includes the same number of images of the same type as the type of examination image included in the examination data Q, from the storage unit 50 using the information of DICOM tags. Types of examination images obtained from DICOM tags include CT images, MRI images, PET images, ultrasound images, simple X-ray images, endoscopic images, and the like. For example, in a case where the examination data Q includes two CT images, three MRI images, and one simple X-ray image, the sample examination data P including two CT images, three MRI images, and one simple X-ray image is searched for.

(2) The sample examination selection means 37 searches for examination items of examinations performed in blood test or urinalysis, examination items of vital data (body temperature, heart rate, electrocardiogram, and the like), and the like from the archive system 10, and selects only the sample examination data P, in which examination items of examinations performed on a patient to be examined are the same as examination items performed on a patient of the sample examination data P, from the sample examination data P searched for in (1).

(3) From the sample examination data P narrowed down in (1) and (2), the sample examination data P having high similarity with the examination data Q is specified. First, using the association means 39, association between the sample image p forming each piece of sample examination data P and the examination image q forming the examination data Q is performed for each of the pieces of sample examination data P narrowed down in (1) and (2), and the similarity between each piece of sample examination data P and the examination data Q is calculated.

The association means 39 includes similarity acquisition means 40 and adjustment value acquisition means 41, and selects the examination image q similar to the sample image of the sample examination data P from the examination data Q using the similarity between the sample image p and the examination image q and an adjustment value for adjusting the similarity and performs association therebetween.

In the case of associating the sample image p included in the sample examination data P with the examination image q included in the examination data Q, two or more examination images q are not associated with one sample image p. Accordingly, in a case where the number of examination images q included in the examination data Q is smaller than the number of sample images p arranged in the layout, there may be no examination image q associated with the sample image p. The same examination image q is not associated with two or more sample images p. That is, the number of examination images q associated with the sample image p is one or less, and the number of sample images p associated with the examination image q included in the examination data Q is also one or less.

The similarity acquisition means 40 calculates a similarity for each combination of one of the sample images p included in the sample examination data P and one of the examination images q included in the examination data Q. The similarity is obtained from the pixel data of the sample image p and the examination image q. Specifically, the similarity is acquired using cross-correlation of pixel data, histogram intersection, and the like. Pixel data refers to a group of pixels forming an image, and supplementary information of an image, such as a DICOM tag, a file name, and imaging date and time, will be described below so as to be distinguished from the pixel data.

The similarity acquisition means 40 acquires a similarity only for the examination image p and the sample image q captured by the same type of modality 2 with reference to the supplementary information, such as the DICOM tag. However, in a case where the examination image p and the sample image q are tomographic images, the similarity between pixel data of the sample image p and the examination image q in different cross-sectional directions, such as an axial cross-section and a sagittal cross-section, may be high even though the examination image p and the sample image q are images captured by the same type of modality 2. Therefore, a cross-sectional direction is determined with reference to the DICOM tag, and a similarity is calculated so that the similarity between the sample image p and the examination image q increases in a case where the cross-sectional directions of a tomographic image included in the sample image p of the layout and a tomographic image included in the examination image q of the examination data Q are the same and the similarity between the sample image p and the examination image q decreases in a case where the cross-sectional directions are not the same.

In two combinations for which the similarity has been calculated, the adjustment value acquisition means 41 calculates an adjustment value of the similarity based on the relationship between the sample image p included in a first combination a and the sample image p included in a second combination b and the relationship between the examination image q included in the first combination a and the examination image q included in the second combination b.

In the case of images before and after administration of a contrast medium that are obtained by imaging the same part, the similarity between images before the administration and the similarity between images after the administration should be high even between the sample image p and the examination image q. However, there is a possibility that the similarity between the sample image p before the administration and the examination image q after the administration will become high depending on how the image contrast medium is diffused. It may be difficult to determine corresponding images only with the similarity of pixel data, such as a plurality of images having different cardiac beat phases of the heart. Therefore, in a case where the relationship between the imaging times of the two sample images p included in the combinations a and b is the same as the relationship between the imaging times of the two examination images q included in the combinations a and b, the adjustment value is set to a value such that the similarity is higher than that in a case where the relationship between the imaging times of the two sample images p included in the combinations a and b is not the same as the relationship between the imaging times of the two examination images q included in the combinations a and b.

Figure 4:
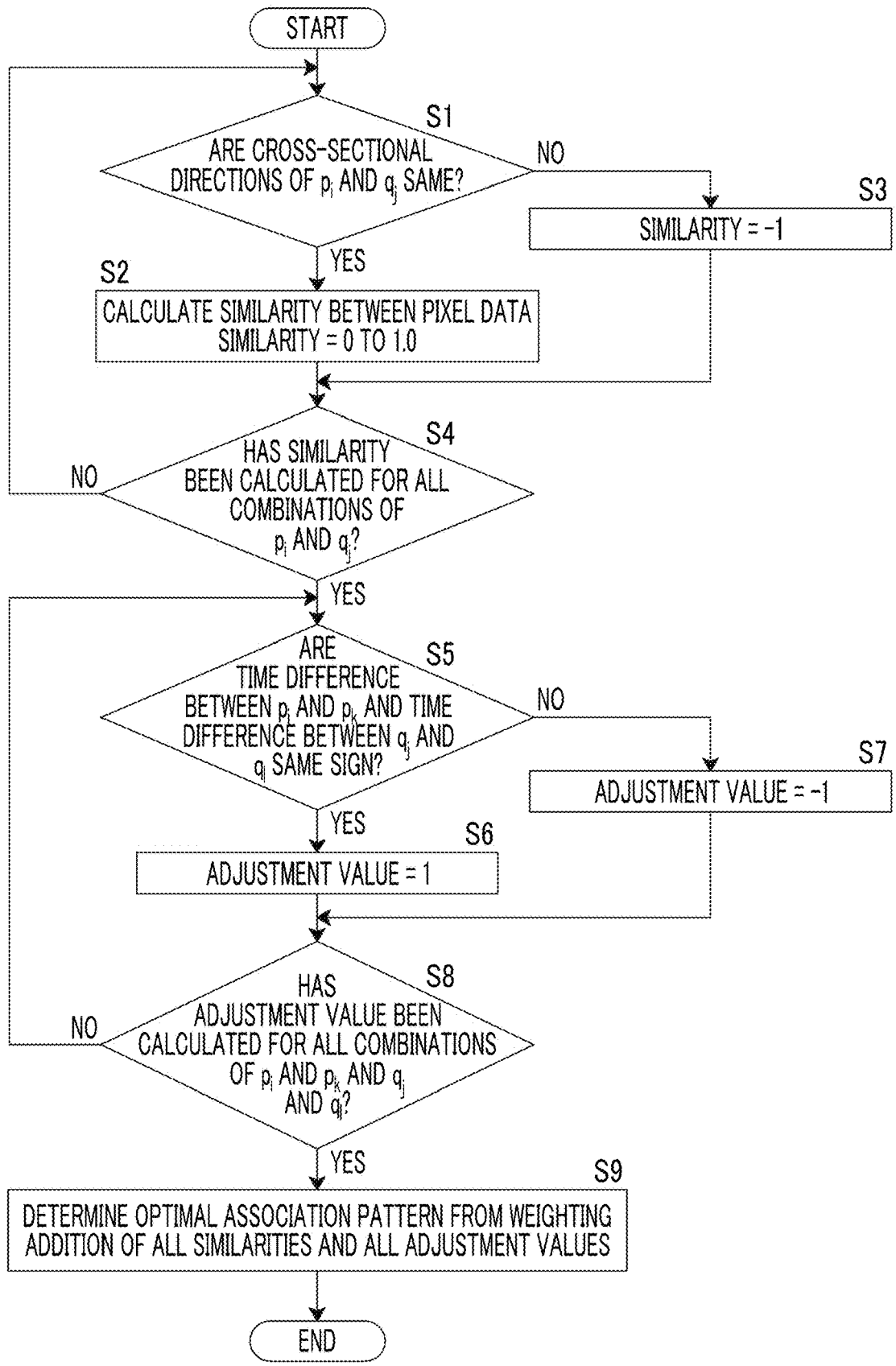
FIG. 4 is a flowchart of a process for associating a sample image and an examination image with each other.
Figure 5:
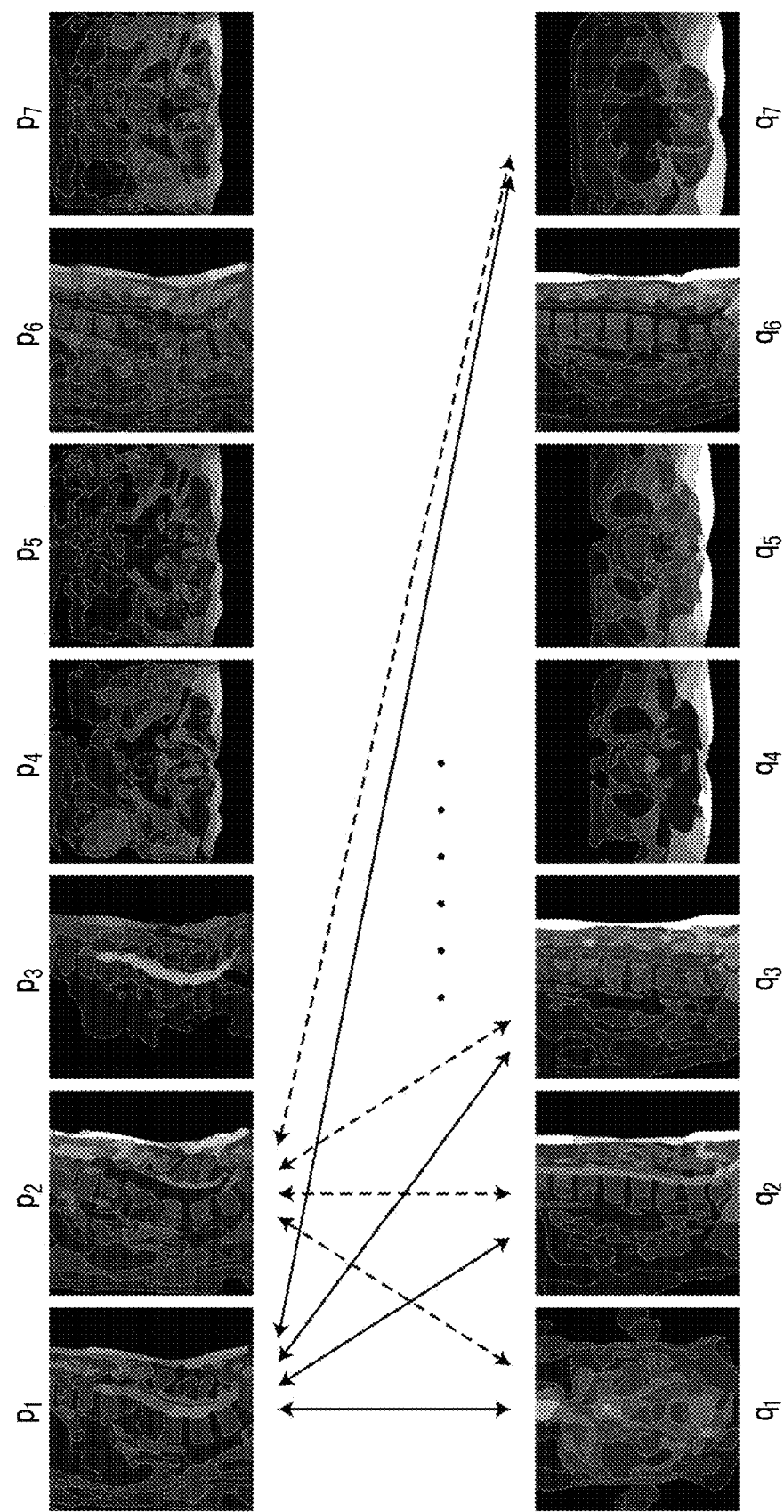
FIG. 5 is a diagram showing examples of a sample image and an examination image.

A process in which the association means 39 associates the sample image p of each piece of sample examination data P with the examination image q of the examination data Q using the similarity and the adjustment value will be specifically described with reference to the flowchart of FIG. 4. FIG. 5 shows examples of sample images $p_1$ to $p_7$ and examination images $q_1$ to $q_7$.

First, the similarity acquisition means 40 calculates a similarity between a sample image $p_i$ that is an element of the sample examination data P and an examination image $q_j$ that is an element of the examination data Q using a histogram intersection. As shown in FIG. 5, in a case where the sample images $p_1$ to $p_7$ and the examination images $q_1$ to $q_7$ are present, the similarity is calculated for all combinations of the sample images $p_1$ to $p_7$ and the examination images $q_1$ to $q_7$. That is, a similarity between $p_1$ and each of $q_1, q_2, q_3, \ldots q_7$ is calculated, and a similarity between $p_2$ and each of $q_1, q_2, q_3, \ldots, q_7$ is calculated. Similarly, a similarity between each of $p_3$ to $p_7$ and each of $q_1, q_2, q_3, \ldots q_7$ is calculated.

In the case of the sample image p and the examination image q having different types of modalities 2, the similarity is set to 0. For example, the similarity between the MRI image and the CT image is set to 0. However, since both the T1-weighted image and the T2-weighted image of MRI images captured by using different types of imaging protocols in the MRI apparatus are MRI images, the similarity is calculated using the histogram intersection.

Figure 6:
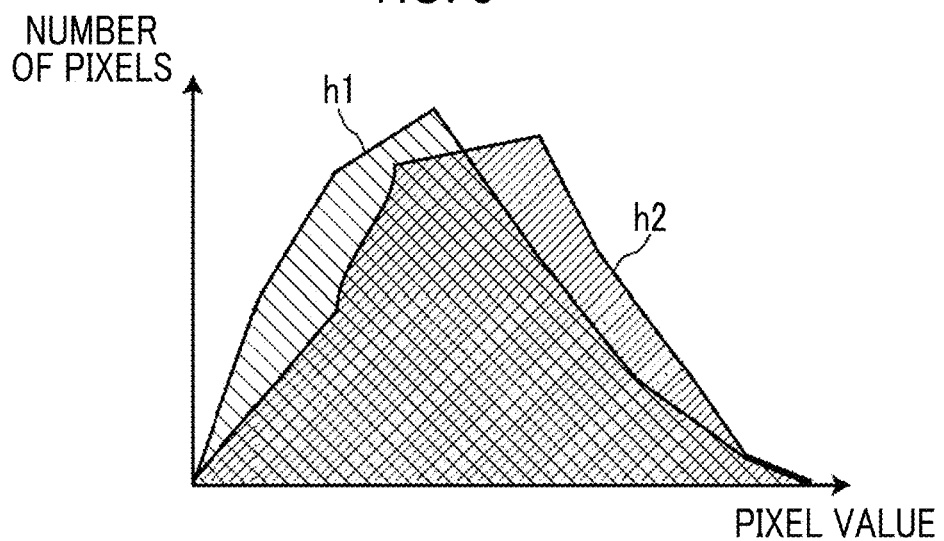
FIG. 6 is a diagram illustrating a method of calculating a similarity from histogram intersection.
Figure 7:
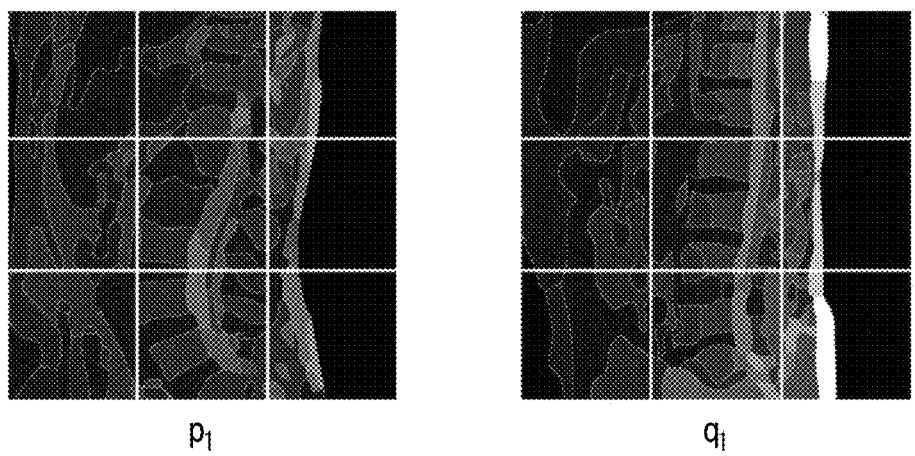
FIG. 7 is a diagram illustrating a method of calculating a similarity reflecting the composition of a screen.

The cross-sectional directions of the sample image $p_i$ and the examination image $q_j$ can be determined based on the description of "Image Orientation" of the DICOM tag, for example. For example, in a case where the sample image $p_i$ is an axial cross-section perpendicular to the body axis, "first row" and "first column" of "Image Orientation" almost match (1, 0, 0) and (0, 1, 0), respectively. Therefore, the degree of matching between two vectors obtained by referring to "Image Orientation" of the examination image $q_j$ and the two vectors (1, 0, 0) and (0, 1, 0) of the sample image $p_i$ is calculated using an inner product operation. In a case where the cross-sectional directions of the sample image $p_i$ and the examination image $q_j$ are the same (S1—Yes), as a similarity between pixel data, as shown in FIG. 6, a ratio (histogram intersection) of the intersection between a histogram h1 of the sample image $p_i$ and a histogram h2 of the examination image $q_j$ is calculated as a similarity $\theta_a$ (S2). In this case, the similarity $\theta_a$ is a value of 0 to 1.0. In order to reflect the rough composition of the screen, for example, each image of the sample image $p_i$ and the examination image $q_j$ may be equally divided into three regions vertically and horizontally (refer to FIG. 7), a histogram intersection may be calculated in each divided section of 3×3 sections (=nine sections), and the average value may be set as the similarity $\theta_a$. On the other hand, in a case where the cross-sectional directions of the sample image $p_i$ and the examination image $q_j$ are different (S1—No), the similarity $\theta_a$ is set to −1 (S3). This is calculated for all combinations of $p_i$ and $q_j$ (S4).

Then, the adjustment value acquisition means 41 calculates an adjustment value $\theta_{ab}$ of the similarity in a case where the sample image $p_i$ and the examination image $q_j$ are associated with each other. The sample image $p_i$ and the examination image $q_j$ are associated with each other such that the number of examination images $q_j$ associated with the sample image $p_i$ is one or less and the number of sample images $p_i$ associated with the examination image $q_j$ included in the examination data Q is also one or less. Which association among all association patterns in the case of performing association so as to satisfy the association conditions is optimal is adjusted based on not only the similarity $\theta_a$ between the pixel data of the sample image $p_i$ and the pixel data of the examination image $q_j$ but also the relationship between the imaging times.

In a case where the examination image $q_j$ is associated with the sample image $p_i$ and the examination image $q_l$ is associated with the sample image $p_k$ between the sample examination data P and the examination data Q, the adjustment value $\theta_{ab}$ is calculated from the combination a of the sample image $p_i$ and the examination image $q_j$ and the combination b of the sample image $p_k$ and the examination image $q_l$. In a case where the sign of a difference ($T_a=t(p_k)-t(p_i)$) between the imaging time $t(p_i)$ of the sample image $p_i$ and the imaging time $t(p_k)$ of the sample image $p_k$ is the same as the sign of a difference ($T_b=t(q_k)-t(q_j)$) between the imaging time $t(q_j)$ of the examination image $q_j$ and the imaging time $t(q_l)$ of the examination image $q_l$ (S5—Yes), the adjustment value $\theta_{ab}$ is set to 1 (S6). In a case where the sign of the difference $T_a$ and the sign of the difference $T_b$ are not the same (S5—No), the adjustment value $\theta_{ab}$ is set to −1 (S7). This is calculated for all the two combinations a and b in each association pattern (S8).

Figure 8A:
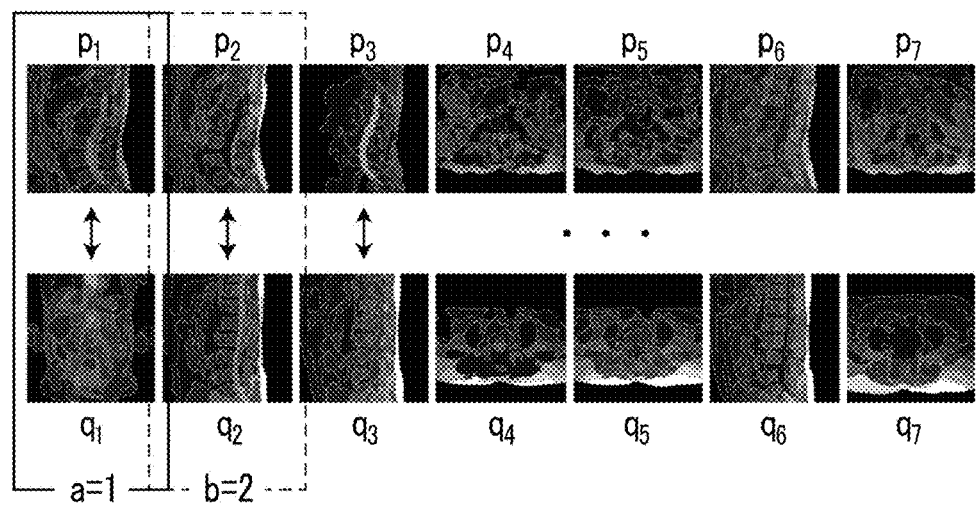
FIGS. 8A to 8C are diagrams illustrating a method of calculating an adjustment value.
Figure 8B:
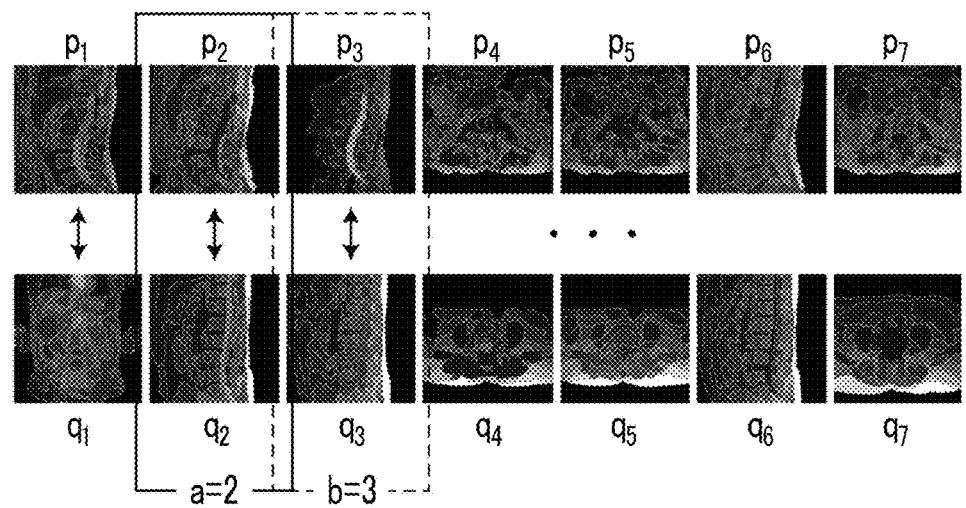
Figure 8C:
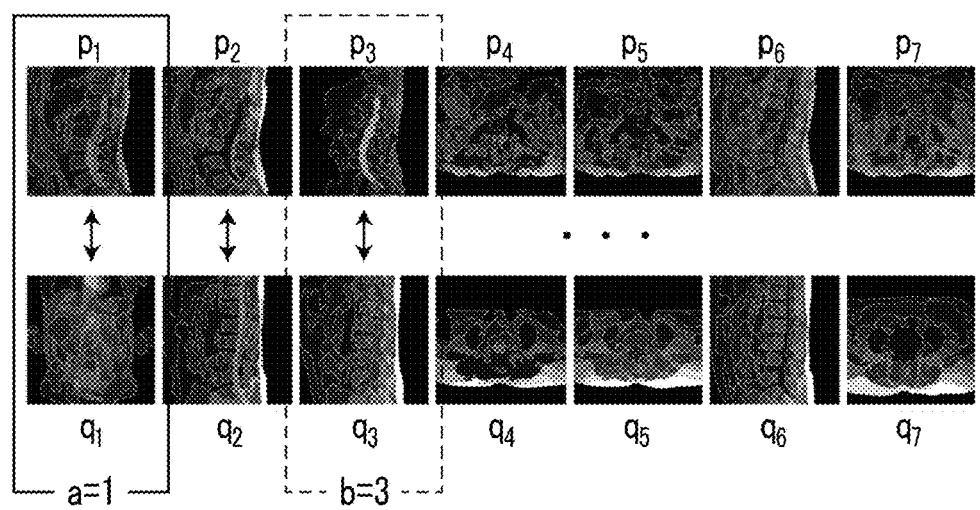

For example, as shown in FIGS. 8A and 8B, in the case of associating $p_1$ and $q_1$, $p_2$ and $q_2$, $p_3$ and $q_3$, . . . , in a case where the difference between the imaging times of $p_1$ and $p_2$ and the difference between the imaging times of $q_1$ and $q_2$ are the same in the combination 1 of $p_1$ and $q_1$ and the combination 2 of $p_2$ and $q_2$ (FIG. 8A), the adjustment value $\theta_{a=1, b=2}$ is set to 1. In the combination 2 of $p_2$ and $q_2$ and the combination 3 of $p_3$ and $q_3$ (FIG. 8B), in a case where the difference between the imaging times of $p_2$ and $p_3$ and the difference between the imaging times of $q_2$ and $q_3$ are not the same, the adjustment value $\theta_{a=2, b=3}$ is set to −1. In the combination 1 of $p_1$ and $q_1$ and the combination 3 of $p_3$ and $q_3$ (FIG. 8C), in a case where the difference between the imaging times of $p_1$ and $p_3$ and the difference between the imaging times of $q_1$ and $q_3$ are the same, the adjustment value $\theta_{a=1, b=3}$ is set to 1. In this manner, the adjustment value $\theta_{ab}$ is calculated for all the two combinations.

Figure 9:
FIG. 9 is a diagram illustrating association between a set of sample images and a set of examination images.

As shown in FIG. 9, between the sample examination data P and the examination data Q, association between the sample image $p_i$ and the examination image $q_j$ is expressed with an association matrix m of elements of P×Q using binary data x of 0 and 1. In the association matrix m, the row indicates the sample image $p_i$ and the column indicates the examination image $q_j$. An element $x_{ij}$ in the i-th row and the j-th column indicates whether or not to associate the sample image $p_1$ with the examination image $q_j$. The element $x_{ij}$ in the i-th row and the j-th column is set to 0 in a case where the sample image $p_1$ is associated with the examination image $q_j$, and is set to 1 in a case where the sample image $p_i$ is not associated with the examination image $q_j$. In this case, all association patterns that associate the sample image $p_i$ and the examination image $q_j$ with each other are created so as to satisfy the conditions in which at most one examination image $q_j$ is associated with the sample image $p_i$ and at most one sample image $p_i$ is associated with the examination image $q_j$ in the sample examination data P and the examination data Q.

A set M of association patterns expressed by the association matrix m can be expressed by the following Equation (1).

$$M = \left\{ x \in \{0, 1\}^{P \times Q} \middle| \sum_{p \in P} x_{pq} \leq 1, \sum_{q \in Q} x_{pq} \leq 1 \right\} \quad (1)$$

In all the patterns that associate the sample image $p_i$ and the examination image $q_j$ included in the set M with each other, a pattern in which the sum of the similarity between the sample image $p_i$ and the examination image $q_j$ associated between the sample examination data P and the examination data Q is the highest is determined as an optimal association pattern between the sample image $p_i$ and the examination image $q_j$ (S9). This can be replaced with a problem of maximizing the following Equation (2) in which the similarity $\theta_a$ calculated by the similarity acquisition means 40 and the adjustment value $\theta_{ab}$ calculated by the adjustment value acquisition means 41 are weighted and added. For example, this problem can be solved using the graph matching method described in the document "L. Torresani, V. Kolmogorov, and C. Rother: "Feature correspondence via graph matching: Models and global optimization", ECCV 2008".

In the following Equation (2), the first term means that all of the similarities $\theta_a$ of the combination of the sample image $p_1$ and the examination image $q_j$ at which $x_{ij}=1$ are added, and the second term means that all the adjustment values $\theta_{ab}$ obtained from the relationship between the two combinations (combination a and combination b) of the sample image $p_i$ and the examination image $q_j$ at which $x_{ij}=1$ in the association matrix m of FIG. 9 are weighted and added. It is preferable that the coefficient K is an empirically optimal value.

$$\max_{x \in M} E(x|\theta) = \sum_{a \in A} \theta_a x_a + k \sum_{(a,b) \in N} \theta_{ab} x_a x_b \qquad (2)$$

Here, A is a set of combinations of the sample image $p_i$ and the examination image $q_j$. N is a set of the combination a of the sample image $p_i$ and the examination image $q_j$ and the combination b of the sample image $p_k$ and the examination image $q_l$. k is a coefficient for determining the load of similarity and adjustment value. $x_a$ is a value of an element $x_{ij}$ corresponding to the combination $a(p_j, q_j)$ in binary data x. $x_b$ is a value of an element $x_{kl}$ corresponding to the combination $a(p_k, q_l)$ in binary data x.

By using the adjustment value $\theta_{ab}$ based on the imaging times of the sample image and the examination image described above, association is performed so that the order of the imaging times of the associated sample images and the order of the imaging times of the associated examination images are not reversed.

As described above, one optimal association pattern between the sample image p included in the sample examination data P and the examination image q included in the examination data Q is determined by the association means 39. The sum of similarities between the sample image p and the examination image q in the association pattern is calculated by the association means 39 (S9).

The similar examination data specifying means 32 determines an optimal association pattern between the sample image p and the examination image q for each of all pieces of sample examination data P narrowed down in (2) by using the association means 39, and calculates the sum of the similarities in the association pattern. The sample examination data P having a high sum of similarities among the pieces of sample examination data P narrowed down in (2) is specified as sample examination data similar to the examination data Q.

Specifically, only one piece of sample examination data P having the highest sum of similarities may be specified as sample examination data similar to the examination data Q. However, a predetermined number of pieces of sample examination data P from the top of the sum of similarities may be specified as sample examination data similar to the examination data Q. Alternatively, the sample examination data P having a similarity equal to or higher than a predetermined threshold value may be specified as sample examination data similar to the examination data Q.

The interpretation reports of the patient of the sample examination data P and the patient of the examination data Q may be read out from the interpretation report database 8, keywords such as information regarding a disease name, the location of a lesion part, and the shape and size of a lesion part may be extracted by performing a known natural language analysis, and the sample examination data P narrowed down in (2), which includes a keyword similar to the interpretation reports of the patient of the sample examination data P and the patient of the examination data Q, may be further narrowed down.

Alternatively, natural language analysis of these interpretation reports may be performed for a plurality of pieces of sample examination data P having a high sum of similarities or the sample examination data P having a sum of similarities equal to or greater than a predetermined threshold value, and the sample examination data P may be further narrowed down based on whether or not a keyword similar to the keyword included in the interpretation report of the patient of the examination data Q is included.

The display means 34 divides the screen of the display 35 according to the layout information L associated with the sample examination data P specified by the similar examination data specifying means 32, and displays the examination image q at an arrangement position, at which the sample image p associated with each examination image q is arranged, according to the association pattern determined by the association means 39.

Although the case where the association means 39 has the similarity acquisition means 40 and the adjustment value acquisition means 41 has been described above, the association means 39 may include only the similarity acquisition means 40 so that the optimal association pattern is determined without using the adjustment value of the similarity in the case of determining the optimal association pattern between the sample image $p_1$ and the examination image $q_j$.

In the case of determining the optimal association pattern from the association patterns associating the sample image $p_i$ and the examination image $q_j$ that are included in the set M described above, an optimal association pattern in which a value obtained by adding all of the similarities $\theta_a$ is the maximum is determined as the optimal association pattern, as shown in the following Equation (3), using only the similarity $\theta_a$ between the sample image $p_i$ and the examination image $q_j$.

$$\max_{x \in M} E(x|\theta) = \sum_{a \in A} \theta_a x_a \qquad (3)$$

Here, A is a set of combinations of the sample image $p_1$ and the examination image $q_j$. $x_a$ is a value of the element $x_{ij}$ corresponding to the combination $a(p_i, q_j)$ in binary data x.

One optimal association pattern between the sample image p and the examination image q is determined between one piece of sample examination data P and one piece of examination data Q by the association means 39, and the sum of similarities between the sample image p and the examination image q in the association pattern is calculated. Using this result, the similar examination data specifying means 32 specifies the sample examination data P having a high sum of similarities, among the pieces of sample examination data P, as sample examination data similar to the examination data Q.

The association means 39 may set a weighting coefficient $w_a$ according to the arrangement position of each sample display layout of sample images included in the sample examination data P and determine an association pattern, in which a value obtained by weighting the similarity $\theta_a$ of the combination a of the sample image $p_i$ and the examination image $q_j$ with the coefficient $w_a$ is the maximum, as an optimal association pattern as shown in the following Equation (4) using a similarity obtained by multiplying the similarity $\theta_a$ of the combination a of the sample image $p_i$ and the examination image $q_j$ by the coefficient $w_a$.

$$\max_{x \in M} E(x|\theta) = \sum_{a \in A} \omega_a \theta_a x_a + k \sum_{(a,b) \in N} \theta_{ab} x_a x_b \qquad (4)$$

Here, A is a set of combinations of the sample image $p_i$ and the examination image $q_j$. N is a set of the combination a of the sample image $p_i$ and the examination image $q_j$ and the combination b of the sample image $p_k$ and the examination image $q_l$. k is a coefficient for determining the load of similarity and adjustment value. $x_a$ is a value of the element $x_{ij}$ corresponding to the combination $a(p_i, q_j)$ in binary data x. $x_b$ is a value of an element $x_{kl}$ corresponding to the combination $a(p_k, q_l)$ in binary data x.

One optimal association pattern between the sample image p and the examination image q is determined between one piece of sample examination data P and one piece of examination data Q by the association means 39, and the sum of similarities between the sample image p and the examination image q in the association pattern is calculated. Using this result, the similar examination data specifying means 32 specifies the sample examination data P having a high sum of similarities, among the pieces of sample examination data P, as sample examination data similar to the examination data Q.

For example, at the time of displaying on the display, the coefficient $w_a$ of the similarity between the sample image q and the examination image p arranged in the upper region is increased to calculate the sum of the similarity $\theta_a$ between the examination data Q and the sample examination data P. Since the similarity between the sample image q and the examination image p at the arrangement position where the coefficient $w_a$ is large influences the sum of the similarities $\theta_a$, the sample image p is preferentially arranged in a region where the coefficient $w_a$ is large. As a result, it is possible to prevent nothing from being displayed in the upper region in the case of displaying the screen in the layout configuration of the sample examination data P.

Alternatively, the coefficient $w_a$ of the similarity $\theta_a$ of the sample image p arranged at the center position for observing the image may be increased. For example, the coefficient $w_a$ of the similarity $\theta_a$ of the sample image p arranged in a large region in a case where the screen is divided may be set to a large value, and the coefficient $w_a$ of the similarity $\theta_a$ of the sample image p arranged in a small region may be set to a small value.

In a case where the layout is configured to include a plurality of pages, the coefficient $w_a$ of the similarity $\theta_a$ of the sample image p arranged on the first page is set to a large value, and the coefficient of the similarity of sample images arranged on the second and third images is gradually reduced to a small value. Alternatively, in the case of displaying on a plurality of displays, the coefficient $w_a$ of the similarity $\theta_a$ of the sample image p arranged on the display installed on the left side may be set to a large value, and the coefficient $w_a$ of the similarity $\theta_a$ of the sample image p arranged on the display installed on the right side may be set to a small value.

Figure 10:
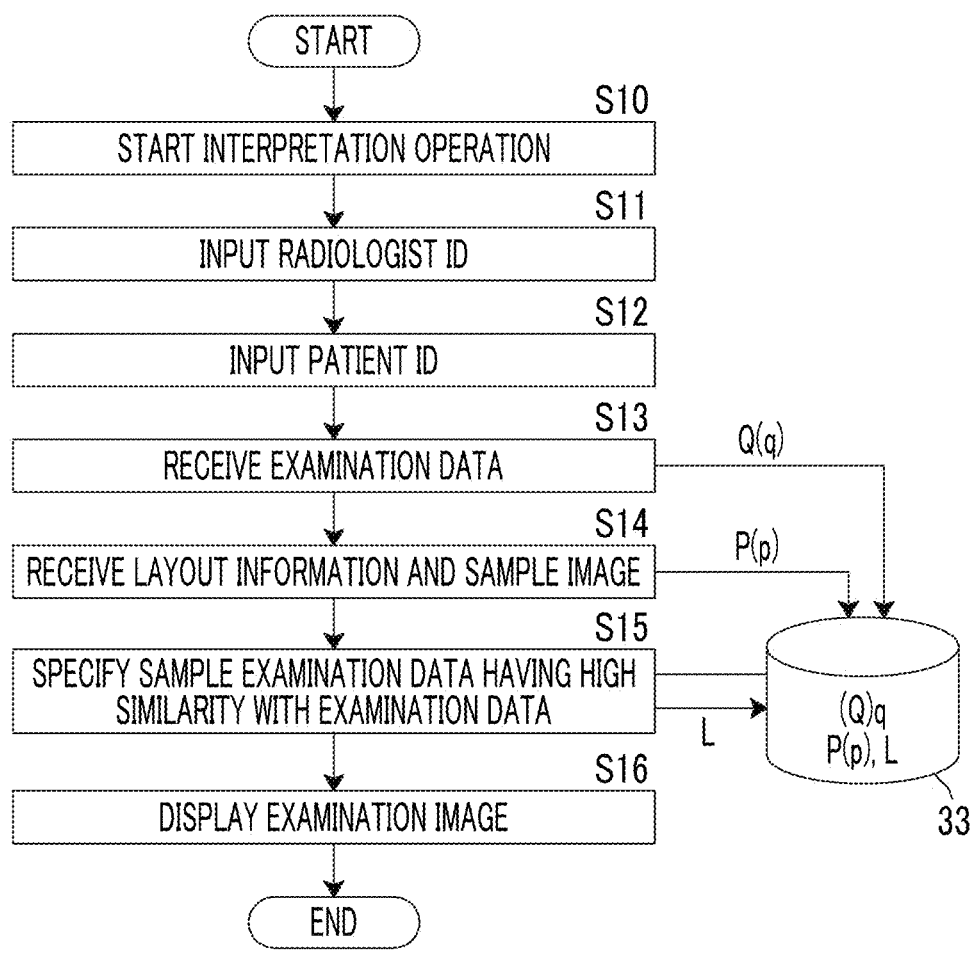
FIG. 10 is a flowchart illustrating the operation of the automatic layout apparatus.

Next, the operation of the automatic layout apparatus of the present embodiment will be described with reference to the flowchart of FIG. 10.

In a case where a radiologist performs an operation for interpretation in the workstation for radiologists 3, an automatic layout program is started (S10). The input radiologist ID is transmitted from the workstation for radiologists 3 to the image management server 5, and examination data can be transmitted and received through authentication of the radiologist ID (S11).

Then, in a case where the radiologist inputs a patient ID of an examination target (S12), the reception means 31 of the workstation for radiologists 3 transmits the patient ID and a request for the viewing of the examination image q to the image management server 5. The image management server 5 searches for the examination image q, to which the patient ID is assigned, from the image database 6 and transmits the examination image q to the workstation for radiologists 3. The reception means 31 stores the received examination image q in the auxiliary storage device 33 as the examination data Q (S13).

(1) First, the sample examination search means 36 requests the image management server 5 to search for the sample examination data P, which includes the same number of images of the same type as the type of the examination image q included in the examination data Q, based on the information of the DICOM tag from the sample examination data P of other patients excluding the patient to be examined. Then, the sample examination selection means 37 selects only the sample examination data P whose examination item for the patient is the same as the examination item of the examination data Q, takes out the sample examination data P from the storage unit 50, and temporarily stores the sample examination data P in the auxiliary storage device 33 of the workstation for radiologists 3 (S14).

Then, the similar examination data specifying means 32 specifies the sample examination data P having high similarity with the examination data Q among the pieces of sample examination data P stored in the auxiliary storage device 33 (S15). In addition, the layout information L corresponding to the sample examination data P specified to have high similarity is read out from the storage unit 50 and stored in the auxiliary storage device 33.

The display means 34 displays the examination image q of the examination data Q on the display 35 according to the layout information L of the sample examination data P having the highest similarity with the examination data Q among the pieces of the sample examination data P. Each examination image q is arranged and displayed at the position of the sample image p associated with the examination image q by the association means 39. In a case where a plurality of pieces of sample examination data P having a high similarity are acquired by the similar examination data specifying means 32, it is preferable that the display means 34 displays a plurality of layouts of sample examination data P on the screen as a list so that the radiologist can select the sample examination data P. Alternatively, reduced images of a plurality of layouts may be displayed on the screen so as to be able to be selected.

Figure 11:
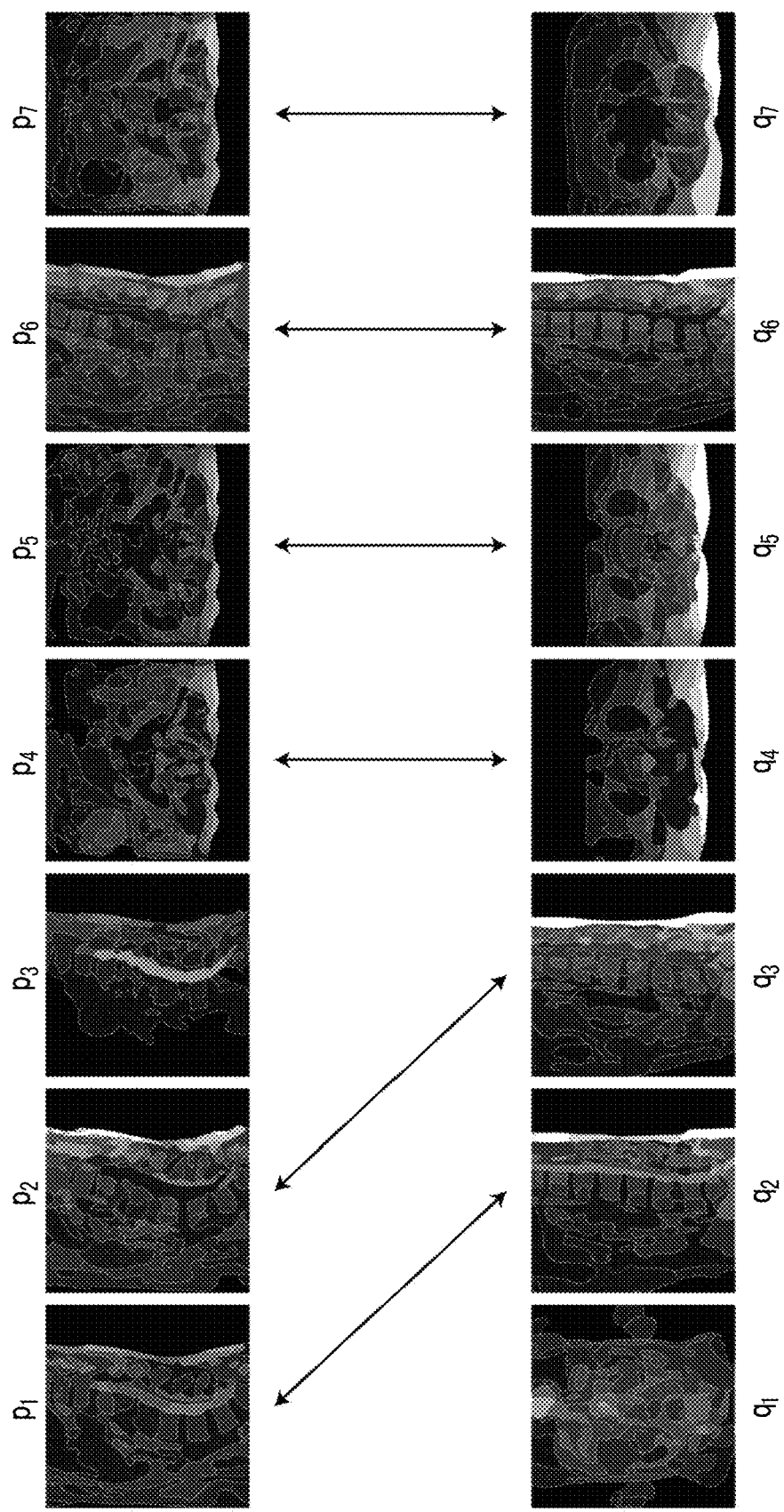
FIG. 11 is a diagram showing an example of an association result between sample images and examination images.
Figure 12:
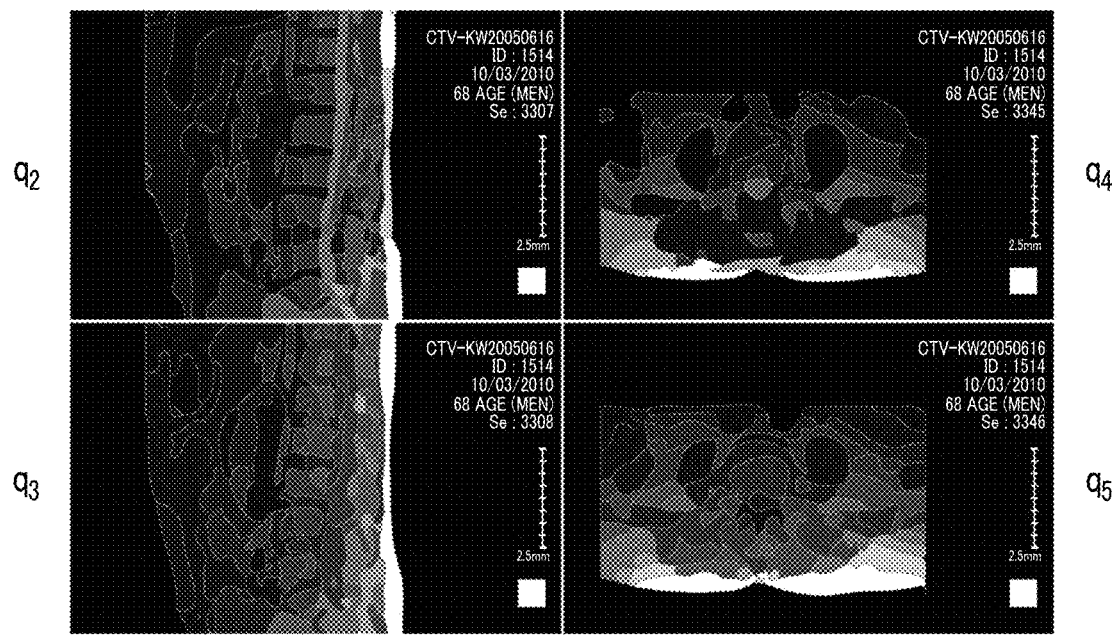
FIG. 12 is a diagram showing an example in which examination images are displayed on a display screen.

In a case where the sample images $p_1$ to $p_7$ are associated with the examination images $q_1$ to $q_7$ in FIG. 5 by the association means 39 as shown in FIG. 11, images are displayed on the display screen as shown in FIG. 12 by the display means 34.

As described in detail above, by automatically selecting sample examination data similar to examination data and arranging the examination image on the screen according to the layout of the sample examination data, it is possible to display an examination image with a layout suitable for diagnosis.

In the layout that could not be determined accurately from supplementary information of an image in the related art, it is possible to perform accurate association between a sample image and an examination image with reference to the sample image. For example, in a case where examination data includes a T1-weighted image and a T2-weighted image of an MR image, different tags are often attached depending on modality vendors or technicians. For this reason, the T1-weighted image and the T2-weighted image of the sample examination data were not accurately associated with each other. However, by associating the T1-weighted image and the T2-weighted image of the sample examination data using the similarity $\theta_a$ between the sample image and the examination image (refer to Equations (1) to (3)), it is possible to realize appropriate association.

In the above description, the case where the association pattern is determined so that the order of the imaging times is the same between the sample image q and the examination image p has been described. However, in a case where a tomographic image is included in the sample image of the layout and a tomographic image is also included in the examination image of the examination data, it is also possible to determine the association pattern so that the order of the positional relationship of the tomographic images is the same between the sample image and the examination image.

In this case, the similarity acquisition means 40 calculates the similarity $\theta_a$ in the same manner as described above. However, in a case where the order of the tomographic position is the same, the adjustment value acquisition means 41 sets the adjustment value to a value that increases the similarity. Specifically, in the case of calculating the adjustment value $\theta_{ab}$ from the combination a of the sample image $p_i$ and the examination image $q_j$ and the combination b of the sample image $p_k$ and the examination image $q_l$, in a case where the sign of a difference $D_1$ between the tomographic positions of the sample image $p_1$ and the sample image $p_k$ is the same as the sign of a difference $D_2$ between the tomographic positions of the examination image $q_j$ and the examination image $q_l$, the adjustment value $\theta_{ab}$ is set to 1. In a case where the sign of the difference $D_1$ and the sign of the difference $D_2$ are not the same, the adjustment value $\theta_{ab}$ is set to −1. By maximizing Equation (2) or (3) that adds the similarity $\theta_a$ and the adjustment value $\theta_{ab}$, it is possible to determine the optimal combination of the sample image $p_1$ and the examination image $q_j$.

As a result, arrangement can be done so that the positional relationship between the tomographic images of the sample images and the positional relationship between the tomographic images of the examination images do not contradict each other.

As described in detail above, in the layout that could not be determined accurately from supplementary information of an image in the related art, it is possible to perform accurate association with reference to a sample image.

In the above description, the case has been described in which the layout information L of the sample examination data P, which is stored in the storage unit 50 and is used in the case of examining a patient other than a patient to be examined, is used in a case where the examination image included in the examination data Q is arranged on the screen. However, the sample examination data P and its layout information L may be prepared in advance and stored in the storage unit 50 or the auxiliary storage device 33 according to the configuration of the display terminal (for example, the above-described workstation for radiologists 3) at the time of interpretation.

For example, in a case where a high-definition display of about 3 MegaPixel (2048×1536) (hereinafter referred to as 3 M display) has a two-screen configuration or in a case where there are one surface of 3 M display and one surface of general display, it is preferable to store the sample examination data P, in which different layouts are defined, in the storage unit 50. Alternatively, in a case where the display terminal is a mobile terminal such as iPad (registered trademark), the sample examination data P in which the layout corresponding to the mobile terminal is defined and the layout information thereof may be prepared in advance and stored in the storage unit 50 or the auxiliary storage device 33.

Alternatively, the medical department workstation 4 may be made to have a function of the automatic layout apparatus of the invention. In this case, the standard sample examination data P corresponding to clinical departments (radiology department, respiratory surgery, orthopedic surgery, and the like) may be stored in the storage unit 50 or the auxiliary storage device 33. In a case where the layout is changed in the case of observing the examination image using the standard sample examination data, the changed layout and the examination image displayed at that time may be newly stored in the storage unit 50 or the auxiliary storage device 33 as the sample examination data P.

Although the case where the storage unit 50 is connected through the network 9 has been described above, the storage unit 50 may be a storage device provided in a computer of the automatic layout apparatus.

What is claimed is:
1. An automatic layout apparatus, comprising:
at least one processor configured to operate as:
a reception means for receiving examination data including a plurality of examination images;
a connection means for communicating with a storage unit that stores layout information, which indicates a layout in which sizes and arrangement positions of a plurality of sample images in a case of arranging the plurality of sample images on a screen are set, so as to be associated with sample examination data including the plurality of sample images; and
a similar examination data specifying means for specifying the sample examination data similar to the examination data using a similarity between each examination image included in the examination data and each sample image included in the sample examination data; and
a display which displays the examination image included in the examination data according to layout information associated with the sample examination data similar to the examination data;
wherein the similar examination data specifying means comprises the processor configured to operate as a similarity acquisition means for acquiring a similarity between the examination image and the sample image for each combination of one of sample images included in the sample examination data and one of examination images included in the examination data, and
in a case where the examination image and the sample image are associated with each other so as to satisfy conditions in which the number of sample images associated with the examination image in the examination data is one or less and the number of examination images associated with the sample image is one or less, the similar examination data specifying means specifies sample examination data similar to the examination data according to a predetermined rule using all the similarities acquired by the similarity acquisition means in a combination of the examination image and the sample image associated with each other.
2. The automatic layout apparatus according to claim 1, wherein the examination data and the sample examination data include images captured by different types of modalities, and the similar examination data specifying means acquires the similarity by associating the sample image and the examination image captured by the same type of modality with each other.

3. The automatic layout apparatus according to claim 1, wherein the examination data and the sample examination data include a plurality of images captured by different types of imaging protocols of a magnetic resonance imaging apparatus.

4. The automatic layout apparatus according to claim 1, wherein the similar examination data specifying means sets a weighting coefficient based on a display position on a layout of each sample image included in the sample examination data, and specifies the sample examination data similar to the examination data using a similarity obtained by multiplying a similarity between each examination image and each sample image by the weighting coefficient of the sample image.

5. The automatic layout apparatus according to claim 1, wherein the similar examination data specifying means further comprises adjustment value acquisition means for acquiring an adjustment value of the similarity based on a relationship between an imaging time of an examination image included in a first combination of two combinations and an imaging time of an examination image included in a second combination and a relationship between an imaging time of a sample image included in the first combination and an imaging time of a sample image included in the second combination, and in a case where the examination image and the sample image are associated with each other so as to satisfy the conditions, the similar examination data specifying means specifies sample examination data similar to the examination data according to a predetermined rule using all the similarities acquired by the similarity acquisition means in a combination of the sample image and the examination image associated with each other and all the adjustment values acquired by the adjustment value acquisition means in the two combinations.

6. The automatic layout apparatus according to claim 5, wherein, in a case where an order of imaging times of a sample image included in the first combination and a sample image included in the second combination is the same as an order of imaging times of an examination image included in the first combination and an examination image included in the second combination, the adjustment value acquisition means sets a value to increase the similarity as the adjustment value.

7. The automatic layout apparatus according to claim 1, wherein a tomographic image is included in a sample image of the layout, a tomographic image is included in an examination image of the examination data, the similar examination data specifying means comprises adjustment value acquisition means for acquiring an adjustment value of the similarity based on a relationship between a tomographic position of a sample image included in a first combination of two combinations and a tomographic position of a sample image included in a second combination and a relationship between a tomographic position of an examination image included in the first combination and a tomographic position of an examination image included in the second combination, and in a case where the sample image and the examination image are associated with each other so as to satisfy the conditions, the similar examination data specifying means specifies sample examination data similar to the examination data according to a predetermined rule using all the similarities acquired by the similarity acquisition means in a combination of the sample image and the examination image associated with each other and all the adjustment values acquired by the adjustment value acquisition means in the two combinations.

8. The automatic layout apparatus according to claim 7, wherein, in a case where an order of tomographic positions of a sample image included in the first combination and a sample image included in the second combination is the same as an order of tomographic positions of an examination image included in the first combination and an examination image included in the second combination, the adjustment value acquisition means sets a value to increase the similarity as the adjustment value.

9. The automatic layout apparatus according to claim 1, wherein the similarity acquisition means acquires the similarity based on a histogram of the examination image and the sample image.

10. The automatic layout apparatus according to claim 1, wherein the examination data includes one or more pieces of electronic document data, and the similar examination data specifying means specifies the sample examination data similar to the examination data based on whether or not a similar keyword is included in electronic document data of the examination data and electronic document data of the sample image data.

11. An automatic layout method in an automatic layout apparatus comprising at least one processor operating as reception means, connection means, similar examination data specifying means, and a display, the method comprising using the at least one processor to perform steps of:

a reception step in which the reception means receives examination data including a plurality of examination images;

a connection step in which the connection means is connected to a storage unit that stores layout information, which indicates a layout in which arrangement positions where a plurality of sample images are arranged on a screen are set, so as to be associated with sample examination data including the plurality of sample images;

a similar examination data specifying step in which the similar examination data specifying means specifies the sample examination data similar to the examination data using a similarity between each examination image included in the examination data and each sample image included in the sample examination data; and a display step in which the display displays the examination image included in the examination data according to layout information associated with the sample examination data similar to the examination data;

wherein the similar examination data specifying step comprises a similarity acquisition step for acquiring a similarity between the examination image and the sample image for each combination of one of sample images included in the sample examination data and one of examination images included in the examination data, and in a case where the examination image and the sample image are associated with each other so as to satisfy conditions in which the number of sample images associated with the examination image in the examination data is one or less and the number of examination images associated with the sample image is one or less, the similar examination data specifying step specifies sample examination data similar to the examination data according to a predetermined rule using all the similarities acquired by the similarity acquisition means in a combination of the examination image and the sample image associated with each other.

12. A non-transitory computer-readable storage medium storing therein an automatic layout program causing a computer to function as:
reception means for receiving examination data including a plurality of examination images;
connection means for being connected to a storage unit that stores layout information, which indicates a layout in which sizes and arrangement positions of a plurality of sample images in a case of arranging the plurality of sample images on a screen are set, so as to be associated with sample examination data including the plurality of sample images;
similar examination data specifying means for specifying the sample examination data similar to the examination data using a similarity between each examination image included in the examination data and each sample image included in the sample examination data; and
display means for controlling a display to display the examination image of the examination data according to layout information associated with the sample examination data similar to the examination data,
wherein the similar examination data specifying means comprises similarity acquisition means for acquiring a similarity between the examination image and the sample image for each combination of one of sample images included in the sample examination data and one of examination images included in the examination data, and
in a case where the examination image and the sample image are associated with each other so as to satisfy conditions in which a number of sample images associated with the examination image in the examination data is one or less and the number of examination images associated with the sample image is one or less, the similar examination data specifying means specifies sample examination data similar to the examination data according to a predetermined rule using all the similarities acquired by the similarity acquisition means in a combination of the examination image and the sample image associated with each other.

* * * * *